US006462039B1

(12) United States Patent
Hillebrand et al.

(10) Patent No.: US 6,462,039 B1
(45) Date of Patent: Oct. 8, 2002

(54) FUNGICIDAL BENZOHETEROCYCLYLOXIME

(75) Inventors: Stefan Hillebrand, Neuss (DE); Bernd-Wieland Krüger, Bergisch Gladbach (DE); Herbert Gayer, Monheim (DE); Peter Gerdes, Aachen (DE); Klaus Stenzel, Düsseldorf (DE); Gerd Hänssler, Leverkusen (DE); Astrid Mauler-Machnik, Leichlingen (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/623,442

(22) PCT Filed: Mar. 8, 1999

(86) PCT No.: PCT/EP99/01472

§ 371 (c)(1),
(2), (4) Date: Sep. 5, 2000

(87) PCT Pub. No.: WO99/46263

PCT Pub. Date: Sep. 16, 1999

(30) Foreign Application Priority Data

Mar. 9, 1998 (DE) .......................................... 198 10 018

(51) Int. Cl.$^7$ ......................... A01N 43/38; A01N 43/56; A01N 43/88; C07D 413/12
(52) U.S. Cl. ...................................... 514/229.2; 544/65
(58) Field of Search .......................... 544/65; 514/229.2

(56) References Cited

U.S. PATENT DOCUMENTS

| 5,679,676 | * 10/1997 | Kruger et al. ............ 514/229.2 |
| 5,935,908 | 8/1999 | Farooq et al. .............. 504/281 |

FOREIGN PATENT DOCUMENTS

| EP | 0 606 489 | 7/1994 |
| WO | 95/04728 | 1/1995 |
| WO | 96/14305 | 5/1996 |
| WO | 96/25406 | 8/1996 |
| WO | 97/07103 | 2/1997 |

\* cited by examiner

*Primary Examiner*—Deepak R. Rao
(74) *Attorney, Agent, or Firm*—Joseph C. Gil

(57) ABSTRACT

The invention relates to novel benzoheterocyclyloximes, to a process for their preparation and to their use as fungicides.

10 Claims, No Drawings

FUNGICIDAL BENZOHETEROCYCLYLOXIME

This application is a 371 of PCT/EP99/01472 filed Mar. 8, 1999.

The invention relates to novel benzoheterocyclyloximes, to a process for their preparation and to their use as fungicides.

It is already known that certain compounds of a similar constitution to those described below have fungicidal properties (compare, for example, WO 95-04 728, WO 96-25 406, WO 97-07 103). However, the fungicidal activity of these compounds is, in particular at low application rates, unsatisfactory.

This invention, accordingly, provides the novel benzoheterocyclyloximes of the general formula (I)

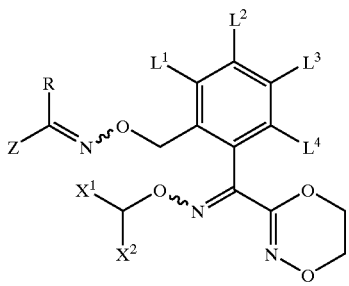

(I)

in which
- $L^1$, $L^2$, $L^3$ and $L^4$ are identical or different and independently of one another each represent hydrogen, halogen, cyano, nitro, in each case optionally halogen-substituted alkyl, alkoxy, alkylthio, alkylsulphinyl or alkylsulphonyl,
- R represents alkyl or optionally substituted cycloalkyl having 3 to 5 carbon atoms,
- $X^1$ and $X^2$ independently of one another represent hydrogen or halogen and
- Z represents optionally substituted benzoheterocyclyl which is attached via the heterocyclyl moiety.

In the definitions, the saturated or unsaturated hydrocarbon chains, such as alkyl, alkenyl or alkinyl, are in each case straight-chain or branched, even in combination with heteroatoms, such as in alkoxy, alkylthio or alkylamino.

Halogen generally represents fluorine, chlorine, bromine or iodine, preferably fluorine, chlorine or bromine, in particular fluorine or chlorine.

Aryl represents aromatic, mono- or polycyclic hydrocarbon rings, such as, for example, phenyl, naphthyl, anthranyl, phenanthryl, preferably phenyl or naphthyl, in particular phenyl.

Heterocyclyl represents saturated or unsaturated, and also aromatic, cyclic compounds in which at least one ring member is a heteroatom, i.e. an atom different from carbon. If the ring contains a plurality of heteroatoms, these can be identical or different. Preferred heteroatoms are oxygen, nitrogen or sulphur.

Benzoheterocyclyl represents a heterocyclic ring having a fused-on benzene ring.

Furthermore, it has been found that the novel benzoheterocyclyloximes of the general formula (I) are obtained when oximes of the general formula (II)

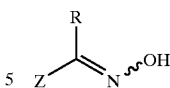

(II)

in which
R and Z are as defined above,
are reacted with a halogenomethyl compound of the general formula (III)

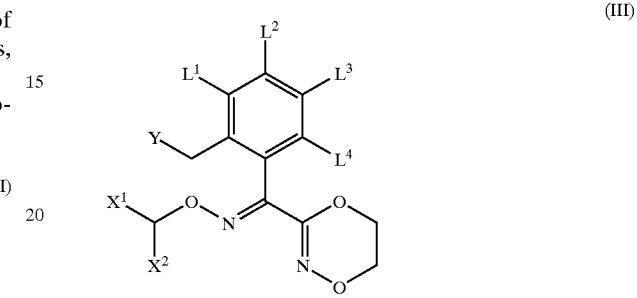

(III)

in which
$L^1$, $L^2$, $L^3$, $L^4$, $X^1$ and $X^2$ are as defined above and
Y represents halogen,
if appropriate in the presence of a diluent and if appropriate in the presence of an acid acceptor.

Finally, it has been found that the novel benzoheterocyclyloximes of the general formula (I) have very strong fungicidal activity.

If appropriate, the compounds according to the invention can be present as mixtures of different possible isomeric forms, in particular of stereolsomers, such as, for example, E and Z, or optical isomers. What is claimed are both the E and the Z isomers, the individual enantiomers, the racemates, and any mixtures of these isomers.

Preference is given to benzoheterocyclyloximes of the formula (Ia), in which

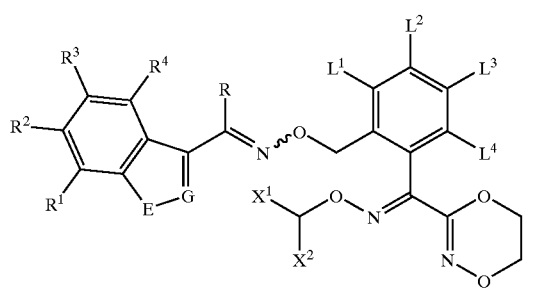

(Ia)

E represents oxygen, sulphur, NH, or N-$R^5$, where
$R^5$ represents alkyl having 1 to 4 carbon atoms, alkenyl or alkinyl having in each case 2 to 4 carbon atoms, where the hydrocarbon groups are in each case optionally substituted by 1 to 5 halogen atoms, or represents benzyl which is optionally mono- to pentasubstituted by halogen, cyano, nitro, alkyl or alkoxy having 1 to 4 carbon atoms, halogenoalkyl or halogenoalkyloxy having 1 to 4 carbon atoms and 1 to 5 halogen atoms,
G represents nitrogen or CH,
$L^1$, $L^2$, $L^3$ and $L^4$ are identical or different and independently of one another each represents hydrogen, halogen, cyano, nitro, represents alkyl, alkoxy, alkylthio, alkylsulphinyl or alkylsulphonyl having in each case 1 to 6 carbon atoms and being in each case optionally substituted by 1 to 5 halogen atoms, preferably represents hydrogen or methyl and in particular represents hydrogen, $X^1$ and $X^2$ independently of one another represent hydrogen, fluorine or chlorine, in particular hydrogen, R represents alkyl having 1 to 4 carbon atoms or cycloalkyl having 3 to 6 carbon atoms and being optionally mono- to tetrasubstituted by halogen or alkyl, preferably represents methyl or cyclopropyl, in particular represents methyl, $R^1$, $R^2$, $R^3$ and $R^4$ are identical or different and independently of one another each represents halogen, cyano, nitro, amino, formyl, carbamoyl, thiocarbamoyl;

in each case straight-chain or branched alkyl, alkoxy, alkoxyalkyl, alkylthioalkyl, alkylaminoalkyl, dialkylaminoalkyl, alkylthio, alkylsulphinyl or alkylsulphonyl having in each case 1 to 8 carbon atoms;

in each case straight-chain or branched alkenyl or alkenyloxy having in each case 2 to 6 carbon atoms;

in each case straight-chain or branched halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms;

in each case straight-chain or branched halogenoalkenyl or halogenoalkenyloxy having in each case 2 to 6 carbon atoms or 1 to 11 identical or different halogen atoms;

in each case straight-chain or branched alkylamino, dialkylamino;

alkylcarbonyl, alkoxycarbonyl, alkylaminocarbonyl, dialkylaminocarbonyl, arylalkylaminocarbonyl, alkenylcarbonyl or alkinylcarbonyl, having 1 to 6 carbon atoms in the respective carbon chains;

cycloalkyl or cycloalkyloxy having in each case 3 to 6 carbon atoms;

or a grouping

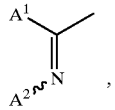

in which
$A^1$ represents hydrogen or alkyl having 1 to 4 carbon atoms or cycloalkyl having 3 to 6 carbon atoms, and
$A^2$ represents hydroxyl, amino, methylamino, methyl, phenyl, benzyl, alkoxy, alkylamino, dialkylamino having 1 to 4 carbon atoms in the respective alkyl chains, or $R^1$ and $R^2$, or $R^2$ and $R^3$, or $R^3$ and $R^4$ together represent alkylene having 3 or 4 carbon atoms, oxyalkylene having 2 or 3 carbon atoms or dioxyalkylene having 1 or 2 carbon atoms, each of which is optionally mono- to tetrasubstituted by identical or different substituents from the group consisting fluorine, chlorine, oxo, methyl, trifluoromethyl and ethyl.

Particular preference is given to benzoheterocyclyloximes of the formula (Ia), in which E represents oxygen, sulphur, NH, or N-$R^5$, where
$R^5$ represents methyl, ethyl, n- or i-propyl, fluoromethyl, difluoromethyl, allyl, propargyl, benzyl or 4-chlorobenzyl, G represents nitrogen or CH, $L^1$, $L^2$, $L^3$ and $L^4$ are identical or different and independently of one another each represents hydrogen, fluorine, chlorine, methyl or methoxy, preferably represents hydrogen or methyl and in particular represents hydrogen, $X^1$ and $X^2$ independently of one another represent hydrogen or fluorine, in particular represent hydrogen, R represents methyl, ethyl, n- or i-propyl, or represents cyclopropyl, cyclobutyl or cyclopentyl, each of which is optionally mono- to tetrasubstituted by fluorine, chlorine, methyl or ethyl, in particular represents methyl, $R^1$, $R^2$, $R^3$ and $R^4$ are identical or different and independently of one another each represents fluorine, chlorine, bromine, cyano, nitro, amino, fonnyl, carbamoyl, thiocarbamoyl, methyl, ethyl, n- or i-propyl, n-, i-, s- or t-butyl, methoxymethyl, methoxy, ethoxy, n- or i-propoxy, methylthio, ethylthio, n- or i-propylthio, methylsulphinyl, ethylsulphinyl, methylsulphonyl or ethylsulphonyl, methylaminomethyl, dimethylaminomethyl, vinyl, allyl, 2-methylallyl, propen-1-yl, crotonyl, propargyl, vinyloxy, allyloxy, 2-methylallyloxy, propen-1-yloxy, crotonyloxy, propargyloxy;

trifluoromethyl, trifluoroethyl, difluoromethoxy, trifluoromethoxy, difluorochloromethoxy, trifluoroethoxy, pentafluoroethoxy, 2-chloro-1,1,2-trifluoroethoxy, difluoromethylthio, trifluoromethylthio, difluorochloromethylthio, trifluoromethylsulphinyl or trifluoromethylsulphonyl, methylamino, ethylamino, n- or i-propylamino, dimetlhylamino, diethylamino, acetyl, propionyl, methoxycarbonyl, ethoxycarbonyl, methylaminocarbonyl, ethylaminocarbonyl, dimethylaminocarbonyl, dimethylaminocarbonyl, acryloyl, propioloyl, cyclopentyl, cyclohexyl, or a grouping

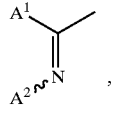

in which
$A^1$ represents hydrogen or methyl and
$A^2$ represents hydroxyl, methoxy, ethoxy, amino, methylamino, methyl, phenyl or benzyl, or $R^1$ and $R^2$, or $R^2$ and $R^3$, or $R^3$ and $R^4$ together represent propanediyl, ethyleneoxy, methyleneoxy, ethylenedioxy, each of which is optionally mono- to tetrasubstituted by identical or different substituents from the group consisting of fluorine, chlorine, oxo, methyl and trifluoromethyl.

$R^1$, $R^2$, $R^3$ and $R^4$ in particular represent hydrogen.

The abovementioned general or preferred radical definitions apply both to the end product of the formula (I) and correspondingly to the starting materials or intermediates required in each case for the preparation.

These radical definitions can be combined with one another as desired, i.e. including combinations between the given ranges of preferred compounds.

The formula (II) provides a general definition of the oximes required as starting materials for carrying out the process according to the invention. In this formula (II), R and Z preferably or in particular have those meanings which have already been mentioned in connection with the description of the compounds of the formula (I) according to the invention as being preferred or as being particularly preferred for R and Z.

Most oximes of the formula (II) are known chemicals for synthesis or can be prepared by customary standard methods (WO 97-07 103, Houben Weyl Volume X/4 (1968) pp. 55 ff). Novel, and also part of the subject-matter of the present application, are oximes of the general formula (II-a),

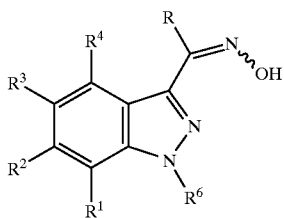

(II-a)

in which
R, $R^1$, $R^2$, $R^3$ and $R^4$ are as defined above and
$R^6$ represents alkyl, alkenyl or alkinyl having 2 to 6 carbon atoms, halogenoalkyl having 1 to 6 carbon atoms and 1 to 13 identical or different halogen atoms or halogenoalkenyl having 2 to 6 carbon atoms and 1 to 11 identical or different halogen atoms.

The oximes of the formula (II-a) are obtained when ketones of the general formula

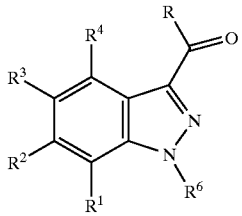

(V)

in which
R, $R^1$, $R^2$, $R^3$, $R^4$ and $R^6$ are as defined above, are reacted with hydroxylamine or an acid addition complex thereof, if appropriate in the presence of a diluent, such as, for example, an alcohol, such as methanol, ethanol, n- or i-propanol, n-, i-, sec- or tert-butanol, mixtures thereof with water or pure water, if appropriate in the presence of a catalyst, such as, for example, triethylamine or sodium acetate.

The formula (V) provides a general definition of the ketones required as starting materials for carrying out the process according to the invention for preparing the oximes of the formula (II-a). In this formula (V), R, $R^1$, $R^2$, $R^3$, $R^4$ and $R^6$ preferably or in particular have those meanings which have already been mentioned in connection with the description of the compounds of the formula (II-a) according to the invention as being preferred or as being particularly preferred for R, $R^1$, $R^2$, $R^3$, $R^4$ and $R^6$.

The ketones of the formula (V) have hitherto not been disclosed. As novel substances, they also form part of the subject-matter of the present application. They are obtained when benzopyrazoles of the formula (VI)

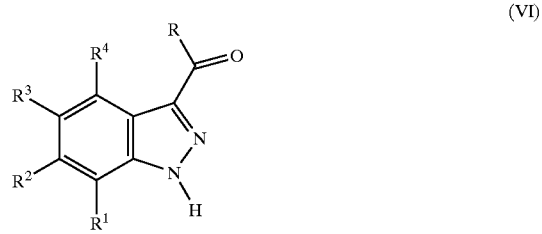

(VI)

in which
R, $R^1$, $R^2$, $R^3$ and $R^4$ are as defined above,
are reacted with an alkylating agent of the general formula (VII)

$R^6$—$X^3$ (VII)

in which
$R^6$ is as defined above, and
$X^3$ represents halogen, alkylsulphonyl, alkyloxysulphonyl or arylsulphonyl,
in if appropriate in the presence of a diluent, an ether, such as diethyl ether, diisopropyl ether, methyl t-butyl ether, methyl t-amyl ether, dioxane, tetrahydrofuran, 1,2-dimethoxyethane, 1,2-diethoxyethane or anisole; a ketone, such as acetone, butanone, methyl isobutyl ketone or cyclohexanone; a nitrile, such as acetonitrile, propionitrile, n- or i-butyronitrile or benzonitrile; an amide, such as N,N-dimethylformamide, N,N-dimethylacetarnide, N-methylformanilide, N-methylpyrrolidone or hexamethylphosphoric triamide; a sulphoxide, such as dimethyl sulphoxide; a sulphone, such as sulpholane; if appropriate in the presence of a base, preferably an alkaline earth metal or alkali metal hydride, hydroxide, amide, alkoxide, carbonate or bicarbonate, such as, for example, sodium hydride, sodium amide, sodium methoxide, sodium ethoxide, potassium tert-butoxide, sodium hydroxide, potassium hydroxide, sodium carbonate, potassium carbonate, potassium bicarbonate, or sodium bicarbonate.

The formula (VI) provides a general definition of the benzopyrazoles required as starting materials for carrying out the process according to the invention for preparing the ketones of the formula (V). In this formula (VI), R, $R^1$, $R^2$, $R^3$ and $R^4$ preferably or in particular have those meanings which have already been mentioned in connection with the description of the compounds of the formula (I) according to the invention as being preferred or as being particularly preferred for R, $R^1$, $R^2$, $R^3$ and $R^4$.

The compounds of the formula (VI) are known or can be prepared by known methods (compare, for example, Chem. Ber. 57, (1924), 1720 or Synthesis 1992, 937 ff).

The formula (VII) provides a general definition of the alkylating agents furthermore required as starting materials for carrying out the process according to the invention for preparing the ketones of the formula (V). In this formula (VII), $R^6$ preferably or in particular has that meaning which has already been mentioned in connection with the description of the compounds of the formula (II-a) according to the invention as being preferred or as being particularly preferred for $R^6$. $X^3$ represents halogen, preferably chlorine, bromine or iodine, or represents alkylsulphonyl, alkyloxysulphonyl or arylsulphonyl, preferably represents methylsulphonyl, methoxysulphonyl or tolylsulphonyl.

The alkylating agents of the formula (VII) are generally known chemicals for synthesis.

The hydroxylamine or its salts furthermore required as starting materials for carrying out the process according to the invention for preparing the oximes of the formula (II-a) arc generally known chemicals for synthesis.

The formula (III) provides a general definition of the halogenomethyl compounds furthermore required as starting materials for carrying out the process according to the invention. In this. formula (III), $L^1$, $L^2$, $L^3$, $L^4$, Q, $X^1$ and $X^2$ preferably or in particular have those meanings which have already been mentioned in connection with the description of the compounds of the formula (I) according to the invention as being preferred or as being particularly preferred for $L^1$, $L^2$, $L^3$, $L^4$, Q, $X^1$ and $X^2$. Y represents halogen, preferably represents chlorine or bromine.

The halogenomethyl compounds of the formula (III) are obtained when, for example, phenoxy compounds of the general formula (IV),

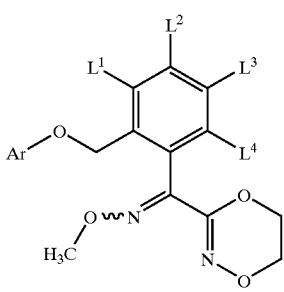

(IV)

in which $L^1$, $L^2$, $L^3$ and $L^4$ are as defined above and

Ar represents optionally substituted phenyl are reacted with a carbonyl halide, such as, for example, acetyl chloride, if appropriate in the presence of a diluent, such as, for example, dichloromethane, and if appropriate in the presence of a Lewis acid, such as, for example, aluminium chloride.

The phenoxy compounds of the formula (IV) are known and/or can be prepared by known methods (compare, for example, WO-A 95-04 728).

Suitable diluents for carrying out the process according to the invention are all inert organic solvents. These preferably include aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzoic, dichloromethane, chloroform, carbon tetrachloride, dichloroethane or trichloroethane, ethers, such as diethyl ether, diisopropyl ether, methyl t-butyl ether, methyl t-amyl ether, dioxane, tetrahydrofuran, 1,2-dimethoxyethane, 1,2-diethoxyethane or anisole; ketones, such as acetone, butanone, methyl isobutyl ketone or cyclohexanone; nitriles, such as acetonitrile, propionitrile, n- or i-butyronitrile or benzonitrile; amides, such as N,N-dimethylfornamide, N,N-dimethylacetamide, N-methylformanilide, N-methylpyrrolidone or hexamethylphosphoric triamide; sulphoxides, such as dimethyl sulphoxide or sulphones, such as sulpholane.

If appropriate, the process according to the invention is carried out in the presence of a suitable acid acceptor. Suitable acid acceptors are all customary inorganic or organic bases. These preferably include alkaline earth metal or alkali metal hydrides, hydroxides, amides, alkoxides, acetates, carbonates or bicarbonates, such as, for example, sodium hydride, sodium amide, sodium methoxide, sodium ethoxide, potassium tert-butoxide, sodium hydroxide, potassium hydroxide, sodium acetate, potassium acetate, calcium acetate, sodium carbonate, potassium carbonate, potassium bicarbonate or sodium bicarbonate, and also tertiary amines, such as trimethylamine, triethylamine, tributylamine, N,N-dimethylaniline, N,N-dimethylbenzylamine, pyridine, N-methylpiperidine, N-methylmorpholine, N,N-dimethylaminopyridine, diazabicyclooctane (DABCO), diazabicyclononene (DBN) or diazabicycloundecene (DBU).

When carrying out the process according to the invention, the reaction temperatures can be varied within a relatively wide range. In general, the process is carried out at temperatures from −20° C. to 180° C., preferably at temperatures from 10° C. to 120° C.

For carrying out the process according to the invention for preparing the compounds of the formula (I), in general from 0.5 to 2 mol, preferably from 0.8 to 1.5 mol, of the halogenomethyl compound of the formula (III) are employed per mole of the oxime of the formula (II).

The process according to the invention is generally carried out under atmospheric pressure. However, it is also possible to operate under elevated or reduced pressure—in general between 0.1 bar and 10 bar.

The practice of the reaction and the work-up and isolation of the reaction products are carried out by generally customary processes (compare also the Preparation Examples).

The compounds according to the invention have a potent microbicidal activity and can be employed for controlling undesirable microorganisms, such as fungi and bacteria, in crop protection and in the protection of materials.

Fungicides are employed in crop protection for controlling Plasmodiophoromycetes, Oomycetes, Chytridiomycetes, Zygomycetes, Ascomycetes, Basidiomycetes and Deuteromycetes.

Bactericides are employed in crop protection for controlling Pseudomonadaceae, Rhizobiaceae, Enterobacteriaceae, Corynebacteriaceae and Streptomycetaceae.

Some pathogens causing fungal and bacterial diseases which come under the generic names listed above are mentioned as examples, but not by way of limitation:

Xanthomonas species, such as, for example, *Xanthomonas campestris* pv. *oryzae;*

Pseudomonas species, such as, for example, *Pseudomonas syringae* pv. *lachrymans;*

Erwinia species, such as, for example, *Erwinia amylovora;*

Pythium species, such as, for example, *Pythium ultimum;*

Phytophthora species, such as, for example, *Phytophthora infestans;*

Pseudoperonospora species, such as, for example, *Pseudoperonospora humuli* or *Pseudoperonospora cubensis;*

Plasmopara species, such as, for example, *Plasmopara viticola;*

Bremia species, such as, for example, *Bremia lactucae,*

Peronospora species, such as, for example, *Peronospora pisi* or *P. brassicae;*

Erysiphe species, such as, for example, *Erysiphe graminis;*

Sphaerotlheca species, such as, for example, *Sphaerotheca fuliginea;*

Podosphaera species, such as, for example, *Podosphaera leucotricha;*

Venturia species, such as, for example, *Venturia inaequalis;*

Pyrenophora species, such as, for example, *Pyrenophora teres* or *P. graminea* (conidia form: Drechslera, syn: Helminthosporium);

Cochliobolus species, such as, for example, *Cochliobolus sativus* (conidia form: Drechslera, syn: Helmilnthosporiuin);

Uromyces species, such as, for example, *Uromyces appendiculatus;*

Puccinia species, such as, for example, *Puccinia recondita;*

Sclerotinia species, such as, for example, *Sclerotinia sclerotiorum*

Tilletia species, such as, for example, *Tilletia caries;*

Ustilago species, such as, for example, *Ustilago nuda* or *Ustilago avenae;*

Pellicularia species, such as, for example, *Pellicularia sasakii;*

Pyricularia species, such as, for example, *Pyricularia oryzae;*

Fusarium species, such as, for example, *Fusarium culmorum;*

Botrytis species, such as, for example, *Botrytis cinerea;*

Septoria species, such as, for example, *Septoria nodorum;*

Leptosphaeria species, such as, for example, *Leptosphaeria nodorum;*

Cercospora species, such as, for example, *Cercospora canescens;*

Alternaria species, such as, for example, *Alternaria brassicae;* and

Pseudocercosporella species, such as, for example, *Pseudocercosporella herpotrichoides.*

The fact that the active compounds are well tolerated by plants at the concentrations required for controlling plant diseases permits the treatment of aerial parts of plants, of propagation stock and seeds, and of the soil.

The active compounds according to the invention can be employed particularly successfully for controlling cereal diseases, such as, for example, against Erysiphe species, Puccinia or Fusarium species, diseases in viticulture and fruit and vegetable growing, such as, for example, against Spaerotheca and Plasmopora species, or rice diseases, such as, for example, against Pyricularia species.

Furthermore, the compounds according to the invention may also be employed to increase the yield of crops. Moreover, they have reduced toxicity and are tolerated well by plants.

Depending on their particular physical and/or chemical properties, the active compounds can be converted into the customary formulations, such as solutions, emulsions, suspensions, powders, foams, pastes, granules, aerosols and microencapsulations in polymeric substances and in coating compositions for seeds, and ULV cool and warm fogging formulations.

These formulations are produced in a known manner, for example by mixing the active compounds with extenders, that is, liquid solvents, liquefied gases under pressure, and/or solid carriers, optionally with the use of surfactants, that is emulsifiers and/or dispersants, and/or foam formers. If the extender used is water, it is also possible to employ, for example, organic solvents as auxiliary solvents. Suitable liquid solvents are essentially: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide or dimethyl sulphoxidc, or else water. Liquefied gaseous extenders or carriers are to be understood as meaning liquids which are gaseous at standard temperature and under atmospheric pressure, for example aerosol propellants such as halogenated hydrocarbons, or else butane, propane, nitrogen and carbon dioxide. Suitable solid carriers are: for example ground natural minerals such as kaolins, clays, talc, chalk, quartz, attapulgite, montmorillonite or diatomaceous earth, and ground synthetic minerals such as highly disperse silica, alumina and silicates. Suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks. Suitable emulsifiers and/or foam formers arc: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates, or else protein hydrolysatcs. Suitable dispersants are: for example lignin-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phosplholipids can be used in the formulations. Other additives can be mineral and vegetable oils.

It is possible to use colorants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 per cent by weight of active compound, preferably between 0.5 and 90%.

Depending on their :particular physical and/or chemical properties, the active compounds can be converted into the customary formulations, such as solutions, emulsions, suspensions, powders, foams, pastes, granules, aerosols and microencapsulations in polymeric substances and in coating compositions for seeds, and ULV cool and warm fogging formulations.

The active compounds according to the invention can be used as such or in their formulations also mixed with known fungicides, bactericides, acaricides, nematicides or insecticides in order thus, for example, to widen the-spectrum of action or to prevent development of resistance. In many cases, synergistic effects are achieved, i.e. the activity of the mixture exceeds the activity of the individual components.

Examples of co-components in mixtures are the following compounds;

Fungicides aldimorph, ampropylfos, ampropylfos potassium, andoprim, anilazine, azaconazole, azoxystrobin, benalaxyl, benodanil, benomyl, benzamacril, benzamacril-isobutyl, bialaphos, binapacryl, biphenyl, bitertanol, blasticidin-S, bromuconazole, bupirimate, buthiobate, calcium polysulphide, capsimycin, captafol, captan, carbendazim, carboxin, carvon, quinomethionate, chlobenthiazone, chlorfenazole, chloroneb, chloropicrin, chlorothalonil, chlozolinate, clozylacon, cufraneb, cymoxanil, cyproconazole, cyprodinil, cyprofuram, debacarb, dichlorophen, diclobutrazole, diclofluanid, diclomezine, dicloran, diethofencarb, difenoconazole, dimethirimol, dimethomorplh, diniconazole, dinicoilazole-M, dinocap, dipheliylamine, dipyrithione, ditalimnfos, dithianon, dodemorplh, dodine, drazoxoloni, edifeniphos, epoxiconazole, etaconazole, ethinimol, etridiazole, famoxadon, fenapanil, fenarimol, fenbuconazole, fenfuram, fenitropan, fenpiclonil, fenpropidin, fenpropimorph, fentin acetate, fentin hydroxide, ferbam, ferimzone, fluazinam, flumetover, fluoromide, fluquinconazole, flurprimidol, flusilazole, flusulfamide, flutolanil, flutriafol, folpet, fosetyl-aluminium, fosetyl-sodium, fthalide, fuberidazole, furalaxyl, furametpyr, furcarbonil, furconazole, furconazole-cis, furmecyclox, guazatine, hexachlorobenzene, hexaconazole, hymexazole, imazalil, imibenconazole, iminoctadine, iminoctadine albesilate, iminoctadine triacetate, iodocarb, ipconazole, iprobenfos (IBP), iprodione, irumamycin, isoprothiolane, isovaledione, kasugamycin, kresoxim-methyl, copper preparations, such as: copper hydroxide, copper naphthenate, copper oxychloride, copper sulphate, copper oxide, oxine-copper and Bordeaux mixture, mancopper, mancozeb, maneb, meferimzone, mepanipyrim, mepronil, metalaxyl, metconazole, methasulfocarb, methfuroxam, metiram, metomeclam, metsulfovax, mildiomycin, myclobutanil, myclozolin, nickel dimethyldithiocarbamate, nitrothal-isopropyl, nuarimol, ofurace, oxadixyl, oxamocarb, oxolinic acid, oxycarboxim, oxyfenthiin, paclobutrazole, pefurazoate, penconazole, pencycuron, phosdiphcn, pimaricin, piperalin, polyoxin, polyoxonim, probenazole, prochloraz, procymidone, propamocarb, propanosine-sodium, propiconazole, propineb, pyrazophos, pyrifenox, pyriniethanil, pyroquilon, pyroxyfur, quinconazole, quintozene (PCNB), sulphur and sulphur preparations, tebuconazole, tecloftalam, tecnazene, tetcyclasis, tetraconazole, thiabendazole, thicyofen, thifluzamide, thiophanate-methyl, thiram, tioxymid, tioxymid, tolclofosmethyl, tolylfluanid, triadimefon, triadimenol, triazbutil, triazoxide, trichlamide, tricyclazole, tridemorph, triflumizole, triforine, triticonazole, uniconazole, validamycin A, vinclozolin, viniconazole, zarilamnide, zineb, zirani and also Dagger G,

OK-8705,

OK-8801,

α-(1,1-dimethylethyl)-β-(2-phenoxyethyl)-1H-1,2,4-triazole-1-ethanol,

α-(2,4-dichlorophenyl)-β-fluoro-b-propyl-1H-1,2,4-triazole-1-ethanol,

α-(2,4-dichlorophenyl)-β-methoxy-a-methyl-1H-1,2,4-triazole-1-ethanol,

α-(5-methyl-1,3-dioxan-5-yl)-β-[[4-(trifluoromethyl)-phenyl]-methylene]-1H-1,2,4-triazole-1-ethanol, (5RS,6RS)-6-hydroxy-2,2,7,7-tetramethyl-5-(1H-1,2,4-triazol-1-yl)-3-octanone, (E)-a-(methoxyimino)-N-methyl-2-phenoxy-phenylacetamide, isopropyl {2-methyl-1-[[[1-(4-methylphenyl)-ethyl]-amino]-carbonyl]-propyl}-carbamate, 1-(2,4-dichlorophenyl)-2-(1H-1,2,4-triazol-1-yl)-ethanone-O-(phenylmethyl)-oxime, 1-(2-methyl-1-naphthalenyl)-1H-pyrrole-2,5-dione, 1-(3,5-dichloroplenyl)-3-(2-propenyl)-2,5-pyrrolidinedione, 1-[(diiodomethyl)-sulphonyl]-4-methyl-benzene, 1-[[2-(2,4-dichlorophenyl)-1,3-dioxolan-2-yl]-methyl]-1H-imidazole, 1-[[2-(4-chlorophenyl)-3-phenyloxiranyl]-methyl]-1H-1,2,4-triazole, 1-[1-[2-[((2,4-dichlorophenyl)-methoxy]-phenyl]-ethenyl]-1H-imidazole, 1-methyl-5-nonyl-2-(phenylmethyl)-3-pyrrolidinole, 2',6'-dibromo-2-methyl-4'-trifluoromethoxy-4'-trifluoromethyl-1,3-thiazole-5-carboxanilide, 2,2-dichloro-N-[1-(4-chlorophenyl)-ethyl]-1-ethyl-3-methyl-cyclopropanecarboxamide, 2,6-dichloro-5-(methylthio)-4-pyrimidinyl-thiocyanate, 2,6-dichloro-N-(4-trinfluoromethylbenzyl)-benzamide, 2,6-dichloro-N-[[4-(trifluoromethyl)-phenyl]-methyl]-benzamide, 2-(2,3,3-triiodo-2-propenyl)-2H-tetrazole, 2-[(1-methylethyl)sulphonyl]-5-(trichloromethyl)-1,3,4-thiadiazole, 2-[[6-deoxy-4-O-(4-O-methyl-β-D-glycopyranosyl)-a-D-glucopyranosyl]-amino]-4-methoxy-1H-pyrrolo[2,3-d]pyrimidine-5-carbonitrile, 2-aminobutane, 2-bromo-2-(bromoinethyl)-pentanedinitrile, 2-chloro-N-(2,3-dihydro-1,1,3-trimethyl-1H-inden-4-yl)-3-pyridinecarboxamide, 2-chloro-N-(2,6-dimethylplienyl)-N-(isothiocyanatomethyl)-acetanide, 2-plienylplhenol (OPP), 3,4-dichiloro-1-[4-(difluoromethoxy)-phenyl]-1H-pyrrole-2,5-dionie, 3,5-dicliloro-N-[cyano-[(1-methyl-2-propynyl)-oxy]-methyl]-benzamide, 3-(1,1-dinicthylpropyl-1-oxo-1H-indene-2-carbonitrile, 3-[2-(4-chlorophenyl)-5-ethoxy-3-isoxazolidinyl]-pyridine, 4-chloro-2-cyano-N,N-dimethyl-5-(4-methylphenyl)-1H-imidazole-1-sulphonamide, 4-methyl-tetrazolo[1,5-a]quinazolin-5(4H)-one, 8-(1,1-dimethylethyl)-N-ethyl-N-propyl-1,4-dioxaspiro[4.5]decane-2-methanamine, 8-hydroxyquinoline sulphate, 9H-xanthene-2-[(phenylamino)-carbonyl]-9-carboxylic hydrazide, bis-(1-methylethyl)-3-methyl-4-[(3-methylbenzoyl)-oxy]-2,5-thiophenedicarboxylate, cis-1-(4-chlorophenyl)-2-(1H-1,2,4-triazol-1-yl)-cycloheptanol, cis-4-[3-[4-(1,1-dimethylpropyl)-phenyl-2-methylpropyl]-2,6-dimethylmorpholinehydrochloride, ethyl [(4-chlorophenyl)-azo]-cyanoacetate, potassium hydrogen carbonate, methanetetrathiol sodium salt, methyl 1-(2,3-dihydro-2,2-dimethyl-1H-inden-1-yl)-1H-imidazole-5-carboxylate, methyl N-(2,6-dimethylphenyl)-N-(5-isoxazolylcarbonyl)-DL-alaninate, methyl N-(chloroacetyl)-N-(2,6-dimethylphenyl)-DL-alaninate, N-(2,3-dichloro-4-hydroxyphenyl)-1-methyl-cyclohexanecarboxamide, N-(2,6-dimethylplienyl)-2-methoxy-N-(tetrahydro-2-oxo-3-furanyl)-acetamide,
N-(2,6-dimethylplienyl)-2-methoxy-N-(tetrahydro-2-oxo-3-thienyl)-acetamide,
N-(2-chloro-4-nitrophenyl)-4-methyl-3-nitro-benzenesulphonamide,
N-(4-cycloexylphenyl)-1,4,5,6-tetrahydro-2-pyrimidinamine,
N-(4-hexylphenyl)-1,4,5,6-tetrahydro-2-pyrimidinamine,
N-(5-chloro-2-methylphenyl)-2-methoxy-N-(2-oxo-3-oxazolinyl)-acetamide,
N-(6-methoxy)-3-pyridinyl)-cyclopropanecarboxamide,
N-[2,2,2-trichloro-1-[(chloroacetyl)-amino]-ethyl]-benzamide,
N-[3-chloro-4,5-bis-(2-propinyloxy)-phenyl]-N'-methoxy-methanimidamide,
N-formyl-N-hydroxy-DL-alanine sodium salt,
O,O-diethyl[2-(dipropylamino)-2-oxoethyl]-ethylphosphoramidothioate,
O-methyl S-phenyl phenylpropylphosphoramidothioate,
S-methyl 1,2,3-benzothiadiazole-7-carbothioate,
spiro[2H]-1-benzopyrane-2,1'(3'H)-isobenzofuran]-3'-one,
Bactericides
bromopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.
Insecticides/Acaricides/Nematicides
abamectin, acephate, acrinathrin, alanycarb, aldicarb, alphamethrin, amitraz, avermectin, AZ 60541, azadirachtin, azinphos A, azinphos M, azocyclotin,
Bacillus thuringiensis, 4-bromo-2-(4-chlorophenyl)-1-(ethoxymethyl)-5-(trifluoromethyl)-1H-pyrrole-3-carbonitrile, bendiocarb, benfuracarb, bensultap, betacyfluthrin, bifenthrin, BPMC, brofenprox, bromophos A, bufencarb, buprofezin, butocarboxim, butylpyridaben,
cadusafos, carbaryl, carbofuran, carbophenothion, carbosulfan, cartap, chloethocarb, chlorethoxyfos, chlorfenapyr, chlorfenvinphos, chlorfluazuron, chlormephos, N-[(6-chloro-3-pyridinyl)-methyl]-N'-cyano-N-methyl-ethanimidamide, chlorpyrifos, chlorpyrifos M, cis-resmethirin, clocythrin, clofentezine, cyanophos, cycloprothrin, cylutlrin, cyhalothrin, cyhexatin, cypermethrin, cyromazine,
deltamnethrin, demeton M, demeton S, demeton S-methyl, diafenthiuron, diazinon, dichlofenthion, dichlorvos, dicliphos, dicrotophos, diethion, diflubenzuron, dimethoate, dimethylvinphos, dioxathion, disulfoton,
edifenphos, emamectin, esfenvalerate, ethiofencarb, ethion, ethofenprox, ethoprophios, etrimphos,
fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, fluazuron, flucycloxuron, flucythrinate, flufenoxuron, flufenprox, fluvalinate, fonophos, formothion, fosthiazate, fubfenprox, furathiocarb,
HCH, heptenophos, hexaflumuron, hexythiazox,
imidacloprid, iprobenfos, isazophos, isofenphos, isoprocarb, isoxathion, ivermectin,
lambda-cyhalothrin, lufenuron,
malathion, mecarbam, mervinphos, mesulfenphos, metaldehyde, methacrifos, methamidophos, methidathion, methiocarb, methomyl, metolcarb, milbemectin, monocrotophos, moxidectin,
naled, NC 184, nitenpyram,
ometghoate, oxamyl, oxydemethon M, oxydeprofos,
parathion A, parathion M, permethrin, phenthoate, phorate, phosalone, phosmet, phosphamidon, phoxini, pirimicarb, pirimiphos M, pirimniphos A, profenophos, prom ecarb, propaphos, propoxur, prothiofos, protthoate, pymetrozitn, pyrachliophos, pyridaphentlhion, pyresmethrin, pyrethrum, pyridaben, pyrimidifen, pyriproxifen,
quinalphos,
salithion, sebufos, silafluofen, sulfotep, sulprofos,
tebufenozide, tebufenpyrad, tebupirimiphos, teflubeazuron, teflutlrin, temephos, terbam, terbufos, tetrachlorvinphos, thiafenox, thiodicarb, thiofanox, thiomethon, thionazin, thuringiensin, tralomethrin, triarathen, triazophos, triazuron, trichlorfon, triflumuron, trimethacarb,
vamidothion, XMC, xylylcarb, zetamethrin.

It is also possible to admix other known active compounds, such as herbicides, fertilizers and growth-regulators.

The active compounds can be used as such or in the form of their commercial formulations or the use forms prepared therefrom, such as ready-to-use solutions, suspensions, wettable powders, pastes, soluble powders, dusts and granules. They are used in the customary manner, for example by pouring, spraying, atomizing, spreading, foaming, brushing on and the like. It is further possible to apply the active compounds by the ultra-low volume method or to inject the active compound formulation, or the active compound itself, into the soil. The seed of the plants can also be treated.

When using the active compounds according to the invention as fungicides, the application rates can be varied within a relatively wide range, depending on the type of application. In the treatment of parts of plants, the application rates of active compounds are generally between 0.1 and 10,000 g/ha, preferably between 10 and 1000 g/ha. In the treatment of seed, the application rates of active compound are generally between 0.001 and 50 g per kilogram of seed, preferably between 0.01 and 10 g per kilogram of seed. In the treatment of the soil, the application rates of active compound are generally between 0.1 and 10,000 g/ha, preferably between 1 and 5000 g/ha.

PREPARATION EXAMPLES:

Example (1)

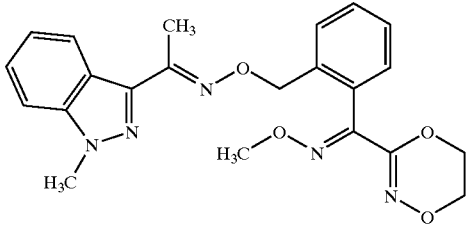

At 20° C., 0.03 g (0.001 mol) of 80% pure sodium hydride is added to a mixture of 0.19 g (0.001 mol) of 1-(1-methyl-1H-indazol-3-yl)-ethanone-oxime and 4 ml of dimethylformamide. This mixture is stirred at 20° C. for 30 minutes and then admixed with 0.27 g (0.001 mol) of O-methyl (2-chloromethyl-phenyl)-(5,6-dihydro-[1,4,2]dioxazin-3-yl)-methanone-oxime. The reaction mixture is stirred at 20° C. for another 16 hours and then dissolved in 30 ml of ethyl acetate and admixed with 50 ml of water. The organic phase is separated off, washed once with in each case 30 ml of 1-molar aqueous sodium hydroxide solution and water, dried over sodium sulphate and concentrated. The residue that remains is chromatographed over silica gel using a mixture of cyclohexane/ethyl acetate (4:1). Concentration of the eluate gives 0.25 g (60% of theory) of O-{2-[(5,6-dihydro-[1,4,2]dioxazin-3-yl)-methoxyiminomethyl]-benzyl}1-(1-methyl-1H-indazol-3-yl)-ethanone-oxime.

$^1$H-NMR spectrum: δ=8.2 (d, 1H, J=8.2 Hz); 7.6 (d, 1H, J=7.2 Hz); 7.4–7.2 (m, 4H); 7.2–7.1 (m, 2H); 5.3 (s, 2H); 4.4 (m, 2H); 4.1 (m, 2H); 4.1 (s, 3H); 4.0 (s, 3H); 2.4 (s, 3H) ppm.

Preparation of the Starting Material

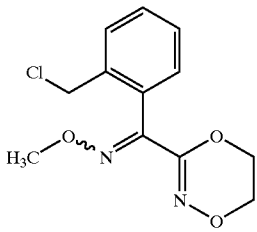

Over a period of 15 min, 61.1 g (0.775 mol) of acetyl chloride are added to a suspension of 103.4 g (0.775 mol) of anhydrous aluminum chloride in 1 l of dichloromethane. Under argon, a solution of 105 g (0.31 mol) of O-methyl (5,6-dihydro-[1,4,2]dioxazin-3-yl)-(2-o-tolyloxymethyl-phenyl)-methanone-oxime in 500 ml of dichloromethane is added dropwise at 20° C. to this mixture, whereupon the reaction mixture warms to 30° C., and stirring is continued for another 3 hours. The reaction mixture is poured into 2 l of ice-water and extracted 3 times with in each case 300 ml of dichloromethane. The combined organic phases are dried over magnesium sulphate and concentrated under reduced pressure. The residue is stirred with diisopropyl ether and the resulting solid is filtered off with suction (59.1 g). The filtrate is concentrated under reduced pressure and the residue is chromatographed over silica gel using cyclohexane/etlhyl acetate (3:1). This gives a further 4 g of product. Overall, 63.1 g (76% of theory) of O-methyl (2-chloromethyl-phenyl)-(5,6-dihydro-[1,4,2]dioxazin-3-yl)-methanone-oxime are obtained.

$^1$H-NMR (CDCl$_3$, TMS): δ=3.99; 4.17–4.20; 4.49–4.53; 7.15–7.53 ppm.

Preparation of Starting Materials According to Formula (II-a)

cExample (II-a-1)

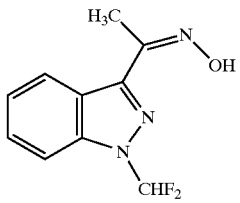

A solution of 0.63 g (0.003 mol) of 1-(1-difluoromethyl-1H-indazol-3-yl)-ethanone 0.626 g (0.009 mol) of hydroxylammonium chloride and 0.9 g of triethylamine in 15 ml of ethanol is heated under reflux at the boil for 4 hours. The mixture we cooled and poured onto 150 g of ice. The crystallized product is filtered off with suction. This gives 0.6 g (89% of theory) of 1-(1-difluoromethyl-1H-indazol-3-yl)-ethanone-oxime.

The following compounds were obtained analogously:

| Example | | LogP |
|---|---|---|
| (II-a-2) | 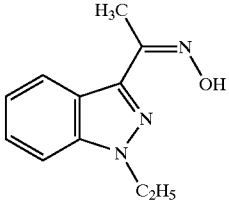 | 2.13 |
| (II-a-3) | 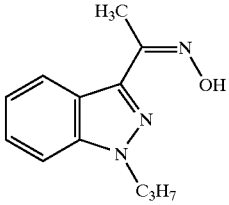 | 2.55 |
| (II-a-4) | 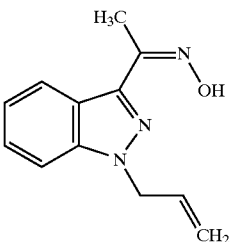 | 2.28 |
| (II-a-5) | 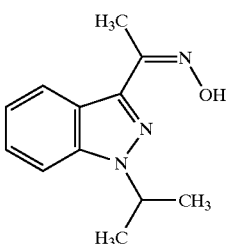 | 2.72 |
| (II-a-6) | 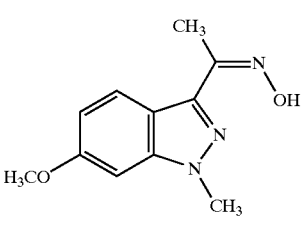 | 1.76 |
| (II-a-7) | 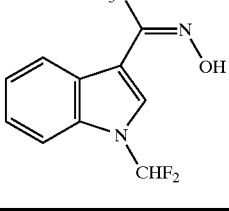 | 2.25 |

Preparation of Starting Materials According to Formula (V)

Example (V-1)

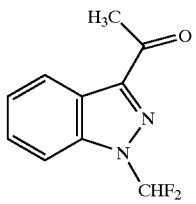

At 70° C., chlorodifluoromethane is introduced for 3 hours into a mixture of 36.8 g (0.23 mol) of 1-(1H-indazol-3-yl)-ethanone and 38.5 g of potassium carbonate in 400 ml of dimethylformamide. The mixture is then poured into 1.5 l of ice-water and the precipitated product is filtered off with suction. The crude product is chromatographed over silica gel using petroleum ether/methyl t-butyl ether (6:1). This gives 27 g (56% of theory) of 1-(1-difluoromethyl-1H-indazol-3-yl)-ethanone. HPLC: logP=2.67

The following compounds were obtained analogously:

| Example | | LogP |
|---|---|---|
| (V-2) | | 2.35 |
| (V-3) | | 2.81 |
| (V-4) | | 2.53 |
| (V-5) | | 2.98 |
| (V-6) | | 1.99 |
| (V-7) | | 2.22 |

The compounds of the formula (I-b) according to the invention listed in Table 1 below are likewise obtained analogously to Example (1) and in accordance with the general description of the preparation process according to the invention:

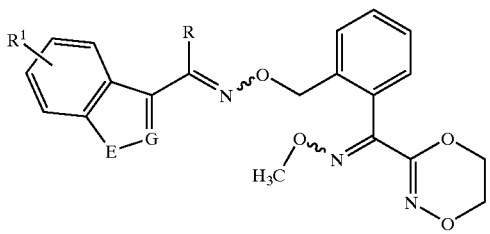

TABLE 1

| Example | E | G | R | logP | R¹ |
|---|---|---|---|---|---|
| 2 | O | N | —CH₃ | 3.52 | H |
| 3 | N(CH₃) | CH | —CH₃ | 3.35 | H |
| 4 | S | CH | —CH₃ | 3.85 | H |
| 5 | N(i-propyl) | N | —CH₃ | 4.23 | H |
| 6 | N—CHF₂ | N | —CH₃ | 3.80 | H |
| 7 | —N—C₂H₅ | CH | —CH₃ | 3.67 | H |
| 8 | S | CH | —CH₃ | 4.05 | H |
| 9 | N(i-propyl) | N | —CH₃ | 3.75 | H |
| 10 | N—CHF₂ | CH | —CH₃ | 3.59 | H |
| 11 | N—(CH₃) | N | —CH₃ | 3.20 | 6-OCH₃ |

The logP values were determined in accordance with EEC Directive 79/831 Annex V. A8 by HPLC (gradient method, acetonitrile/0.1% aqueous phosphoric acid)

USE EXAMPLES:

Example A

Plasmopara Test (Grapevine)/Protective

Solvent: 47 parts by weight of acetone

Emulsifier: 3 parts by weight of alkylaryl polyglycol ether

To produce a suitable preparation of active compound 1 part by weight of active compound is mixed with the stated amounts of solvent and emulsifier and the concentrate is diluted with water to the desired concentration.

To test for protective activity, young plants are sprayed with the preparation of active compound at the stated application rate. After the spray coating has dried on, the plants are inoculated with an aqueous spore suspension of *Plasmopara viticola* and then remain in an incubation cabin at approximately 20° C. and 100% relative atmospheric humidity for 1 day. The plants are then placed in a greenhouse at approximately 21° C. and approximately 90% relative atmospheric humidity for 5 days. The plants are then moistened and placed in an incubation cabin for 1 day.

Evaluation is carried out 6 days after the inoculation. 0% means an efficacy which corresponds to that of the control, whereas an efficacy of 100% means that no infection is observed.

In this test, the active compounds according to the invention listed in Examples 1, 2 and 3 exhibit, at an application rate of 100 g/ha, an efficacy of >85%.

Example B

Sphaerotheca Test (Cucumber)/Protective

Solvent: 47 parts by weight of acetone

Emulsifier: 3 parts by weight of alkylaryl polyglycol ether

To produce a suitable preparation of active compound, 1 part by weight of active compound is mixed with the stated amounts of solvent and emulsifier and the concentrate is diluted with water to the desired concentration.

To test for protective activity, young plants are sprayed with the preparation of active compound at the stated application rate. After the spray coating has dried on, the plants are inoculated with an aqueous spore suspension of *Sphaerotheca fuliginea*. The plants are then placed in a greenhouse at approximately 23° C. and a relative atmospheric humidity of approximately 70%.

Evaluation is carried out 10 days after the inoculation. 0% means an efficacy which corresponds to that of the control, whereas an efficacy of 100% means that no infection is observed.

In this test, the active compounds according to the invention listed in Examples 1, 2 and 3 exhibit, at an application rate of 100 g/ha, an efficacy of >90%.

Example C

Pyricularia Test (Rice)/Protective

Solvent: 2.5 parts by weight of acetone

Emulsifier: 0.06 part by weight of alkylaryl polyglycol ether

To produce a suitable preparation of active compound 1 part by weight of active compound is mixed with the stated amount of solvent and the concentrate is diluted with water and the stated amount of emulsifier to the desired concentration.

To test for protective activity, young rice plants are sprayed with the preparation of active compound at the stated application rate. After the spray coating has dried on, the plants are inoculated with an aqueous spore suspension of *Pyricularia oryzae*. The plants are then placed in a greenhouse at 100% relative atmospheric humidity and 25° C.

Evaluation is carried out 4 days after the inoculation. 0% means an efficacy which corresponds to that of the control, whereas an efficacy of 100% means that no infection is observed.

In this test, the active compounds according to the invention listed in Examples 1, 2 and 3 exhibit, at an application rate of 125 g/ha, an efficacy of 90% or more.

Example D

Erysiphe Test (Barley)/Protective

Solvent: 25 parts by weight of N,N-dimethylacetamide

Emulsifier: 0.6 part by weight of alkylaryl polyglycol ether

To produce a suitable preparation of active compound 1 part by weight of active compound is mixed with the stated amounts of solvent and emulsifier and the concentrate is diluted with water to the desired concentration.

To test for protective activity, young plants are sprayed with the preparation of active compound at the stated application rate.

After the spray coating has dried on, the plants are dusted with spores of *Erysiphe graminis* f.sp. *hordei*.

The plants are placed in a greenhouse at a temperature of approximately 20° C. and a relative atmospheric humidity of approximately 80% to promote the development of mildew pustules.

Evaluation is carried out 7 days after the inoculation. 0% means an efficacy which corresponds to that of the control, whereas an efficacy of 100% means that no infection is observed.

In this test, the active compound according to the invention listed in Example 1 exhibits, at an application rate of 250 g/ha, an efficacy of 100%.

Example E

Erysiphe Test (Barley)/Curative

Solvent: 25 parts by weight of N,N-dimethylacetamide

Emulsifier: 0.6 part of weight of alkylaryl polyglycol ether

To produce a suitable preparation of active compound 1 part by weight of active compound is mixed with the stated amounts of solvent and emulsifier and the concentrate is diluted with water to the desired concentration.

To test for curative activity, young plants are dusted with spores of *Erysiphe graminis* f.sp. *hordei*. 48 hours after the inoculation, the plants are sprayed with the preparation of active compound at the stated application rate.

The plants are placed in a greenhouse at a temperature of approximately 20° C. and a relative atmospheric humidity of approximately 80% to promote the development of mildew pustules.

Evaluation is carried out 7 days after the inoculation. 0% means an efficacy which corresponds to that of the control, whereas an efficacy of 100% means that no infection is observed.

In this test, the active compound according to the invention listed in Example 1 exhibits, at an application rate of 250 g/ha, an efficacy of 100%.

Example F

Fusarium Nivale (Var. Nivale) Test (Wheat)/Protective

Solvent: 25 parts by weight of N,N-dimethylacetamide

Emulsifier: 0.6 part by weight of alkylaryl polyglycol ether

To produce a suitable preparation of active compound 1 part by weight of active compound is mixed with the stated amounts of solvent and emulsifier and the concentrate is diluted with water to the desired concentration.

To test for protective activity, young plants are sprayed with the preparation of active compound at the stated application rate. After the spray coating has dried on, the plants are sprayed with a conidia suspension of *Fusarium nivale* (var. nivale).

The plants are placed in a greenhouse under transparent incubation hoods at a temperature of approximately 15° C. and a relative atmospheric humidity of approximately 100%.

Evaluation is carried out 4 days after the inoculation. 0% means an efficacy which corresponds to that of the control, whereas an efficacy of 100% means that no infection is observed.

In this test, the active compounds according to the invention listed in Examples 1, 2 and 3 exhibit, at an application rate of 250 g/ha, an efficacy of 100%.

Example G

Puccinia Test (Wheat)/Protective

Solvent: 25 parts by weight of N,N-dimethylacetamide

Emulsifier: 0.6 part by weight of alkylaryl polyglycol ether

To produce a suitable preparation of active compound 1 part by weight of active compound is mixed with the stated amounts of solvent and emulsifier and the concentrate is diluted with water to the desired concentration.

To test for protective activity, young plants are sprayed with the preparation of active compound at the stated application rate. After the spray coating has dried on, the plants are dusted with a conidia suspension of *Puccinia recondita*. The plants remain in an incubation cabin at 20° C. and 100% relative atmospheric humidity for 48 hours.

The plants are then placed in a greenhouse at a temperature of approximately 20° C. and a relative atmospheric humidity of 80% to promote the development of rust pustules.

Evaluation is earned out 10 days after the inoculation. 0% means an efficacy which corresponds to that of the control, whereas an efficacy of 100% means that no infection is observed.

In this test, the active compounds according to the invention listed in Examples 1 and 2 exhibit, at an application rate of 250 g/ha, an efficacy of 100%.

What is claimed is:

1. A compounds of the formula (I)

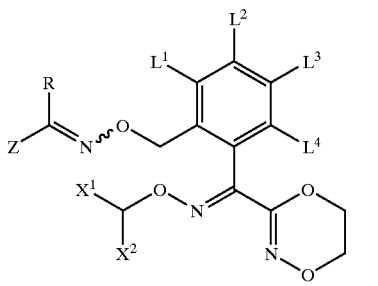

(I)

in which $L^1$, $L^2$, $L^3$ and $L^4$ are identical or different and independently of one another each represent hydrogen, halogen, cyano, nitro, in each case optionally halogen-substituted alkyl, alkoxy, alkylthio, alkylsulphinyl or alkylsulfonyl, R represents alkyl or optionally substituted cycloalkyl having 3 to 5 carbon atoms, $X^1$ and $X^2$ independently of one another represent hydrogen or halogen and Z represents optionally substituted benzoheterocyclyl which is attached via the heterocyclyl moiety.

2. A compound according to claim 1 of the formula (Ia) in which

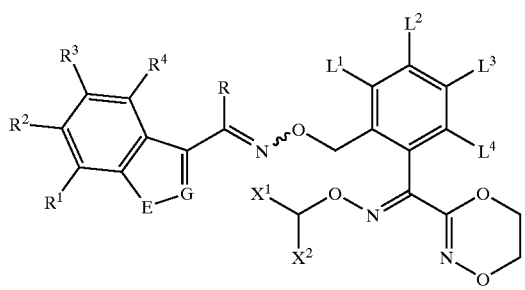

(Ia)

E represents oxygen, sulphur, NH, or N—$R^5$, where
  $R^5$ represents alkyl having 1 to 4 carbon atoms, alkenyl or alkinyl having in each case 2 to 4 carbon atoms, where the hydrocarbon groups are in each case optionally substituted by 1 to 5 halogen atoms, or represents benzyl which is optionally mono- to pentasubstituted by halogen, cyano, nitro, alkyl or alkoxy having 1 to 4 carbon atoms, halogenoalkyl or halogenoalkyloxy having 1 to 4 carbon atoms and 1 to 5 halogen atoms, G represents nitrogen or CH, $L^1$, $L^2$, $L^3$ and $L^4$ are identical or different and independently of one another each represents hydrogen, halogen, cyano, nitro, represents alkyl, alkoxy, alkylthio, alkylsulphinyl or alkylsulphonyl having in each case 1 to 6 carbon atoms and being in each case optionally substituted by 1 to 5 halogen atoms, $X^1$ and $X^2$ independently of one another represent hydrogen, fluorine or chlorine, R represents alkyl having 1 to 4 carbon atoms or cycloalkyl having 3 to 6 carbon atoms and being optionally mono- to tetrasubstituted by halogen or alkyl, $R^1$, $R^2$, $R^3$ and $R^4$ are identical or different and independently of one another each represents
  halogen, cyano, nitro, amino, formyl, carbamoyl, thiocarbamoyl;
  in each case straight-chain or branched alkyl, alkoxy, alkoxyalkyl, alkylthioalkyl, alkylaminoalkyl, dialkylaminoalkyl, alkylthio, alkylsulphinyl or alkylsulphonyl having in each case 1 to 8 carbon atoms;
  in each case straight-chain or branched alkenyl or alkenyloxy having in each case 2 to 6 carbon atoms;
  in each case straight-chain or branched halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms;
  in each case straight-chain or branched halogenoalkenyl or halogenoalkenyloxy having in each case 2 to 6 carbon atoms or 1 to 11 identical or different halogen atoms;
  in each case straight-chain or branched alkylamino, dialkylamino;
  alkylcarbonyl, alkoxycarbonyl, alkylaminocarbonyl, dialkylaminocarbonyl, arylalkylaminocarbonyl, alkenylcarbonyl or alkinylcarbonyl, having 1 to 6 carbon atoms in the respective carbon chains;
  cycloalkyl or cycloalkyloxy having in each case 3 to 6 carbon atoms;

or a grouping

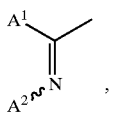

, in which
- $A^1$ represents hydrogen or alkyl having 1 to 4 carbon atoms or cycloalkyl having 3 to 6 carbon atoms, and
- $A^2$ represents hydroxyl, amino, methylamino, methyl, phenyl, benzyl, alkoxy, alkylamino, dialkylamino having 1 to 4 carbon atoms in the respective alkyl chains, or
- $R^1$ and $R^2$, or $R^2$ and $R^3$, or $R^3$ and $R^4$ together represent alkylene having 3 or 4 carbon atoms, oxyalkylene having 2 or 3 carbon atoms or dioxyalkylene having 1 or 2 carbon atoms, each of which is optionally mono- to tetrasubstituted by identical or different substituents from the group consisting fluorine, chlorine, oxo, methyl, trifluoromethyl and ethyl.

3. A compound of the formula (Ia) according to claim 2, in which
- E represents oxygen, sulphur, NH, or N—$R^5$, where
  - $R^5$ represents methyl, ethyl, n- or i-propyl, fluoromethyl, difluoromethyl, allyl, propargyl, benzyl, or 4-chlorobenzyl
- G represents nitrogen or CH,
- $L^1$, $L^2$, $L^3$ and $L^4$ are identical or different and independently of one another each represents hydrogen, fluorine, chlorine, methyl or methoxy,
- $X^1$ and $X^2$ independently of one another represent hydrogen or fluorine,
- R represents methyl, ethyl, n- or i-propyl, or represents cyclopropyl, cyclobutyl or cyclopentyl, each of which is optionally mono- to tetrasubstituted by fluorine, chlorine, methyl or ethyl,
- $R^1$, $R^2$, $R^3$ and $R^4$ are identical or different and independently of one another each represents
  - fluorine, chlorine, bromine, cyano, nitro, amino, formyl, carbamoyl, thiocarbamoyl,
  - methyl, ethyl, n- or i-propyl, n-, i-, s- or t-butyl, methoxymethyl,
  - methoxy, ethoxy, n- or i-propoxy, methylthio, ethylthio, n- or i-propylthio, methylsulphinyl, ethylsulphinyl, methylsulphonyl or ethylsulphonyl,
  - methylaminomethyl, dimethylaminomethyl,
  - vinyl, allyl, 2-methylallyl, propen-1-yl, crotonyl, propargyl, vinyloxy, allyloxy, 2-methylallyl oxy, propen-1-yloxy, crotonyloxy, propargyloxy;
  - trifluoromethyl, trifluoroethyl,
  - difluoromethoxy, trifluoromethoxy, difluorochloromethoxy, trifluoroethoxy, pentafluoroethoxy, 2-chloro-1,1,2-trifluoroethoxy, difluoromethylthio, trifluoromethylthio, difluorochloromethylthio, trifluoromethylsulphinyl or trifluoromethylsulphonyl,
  - methylamino, ethylamino, n- or i-propylamino, dimethylamino, diethylamino,
  - acetyl, propionyl, methoxycarbonyl, ethoxycarbonyl, methylaminocarbonyl, ethylaminocarbonyl, dimethylaminocarbonyl, diethylaminocarbonyl, acryloyl, propioloyl,
  - cyclopentyl, cyclohexyl,
  - or a grouping

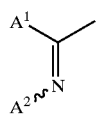

where
- $A^1$ represents hydrogen or methyl and
- $A^2$ represents hydroxyl, methoxy, ethoxy, amino, methylamino, methyl, phenyl or benzyl, or
- $R^1$ and $R^2$, or $R^2$ and $R^3$, or $R^3$ and $R^4$ together represent propanediyl, ethyleneoxy, methylenedioxy, ethylenedioxy, each of which is optionally mono- to tetrasubstituted by identical or different substituents from the group consisting of fluorine, chlorine, oxo, methyl and trifluoromethyl.

4. The compound of claim 2, wherein
- $L^1$, $L^2$, $L^3$ and $L^4$ are identical or different and independently of one another each represents hydrogen or methyl
- $X^1$ and $X^2$ each represent hydrogen, and
- R represents methyl or cyclopropyl.

5. The compound of claim 2, wherein
- $L^1$, $L^2$, $L^3$ and $L^4$ each represent hydrogen, and
- R represents methyl.

6. The compound of claim 3, wherein
- $R^5$ represents methyl or i-propyl,
- $L^1$, $L^2$, $L^3$ and $L^4$ are identical or different and independently of one another each represents hydrogen or methyl, and
- $X^1$ and $X^2$ each represent hydrogen.

7. The compounds of claim 6, wherein
- $L^1$, $L^2$, $L^3$ and $L^4$ each represents hydrogen.

8. A composition for controlling undesirable microorganisms, characterized in that it comprises at least one compound of the formula (I) according to claim 1.

9. Process for preparing a composition for controlling undesirable microorganisms, characterized in that a compound of the formula (I) according to claim 1 is mixed with extenders and/or surfactants.

10. Method for controlling undesirable microorganisms, characterized in that a compound of the formula (I) according to claim 1 is allowed to act on the microorganisms and/or their habitat.

* * * * *